United States Patent [19]

Gall

[11] 4,408,049

[45] Oct. 4, 1983

[54] SUBSTITUTED PIPERAZINYL-1,2,4-TRIAZOLES

[75] Inventor: Martin Gall, Kalamazoo, Mich.

[73] Assignee: The Upjohn Company, Kalamazoo, Mich.

[21] Appl. No.: 362,445

[22] Filed: Mar. 26, 1982

Related U.S. Application Data

[62] Division of Ser. No. 187,920, Sep. 17, 1980, Pat. No. 4,338,453.

[51] Int. Cl.³ .................. C07D 401/00; C07D 403/00; A61K 31/41
[52] U.S. Cl. .................. 544/360; 544/366; 548/262; 548/263; 548/333; 548/336; 424/250; 546/193; 546/210
[58] Field of Search .................. 544/360, 366; 548/262

[56] References Cited

U.S. PATENT DOCUMENTS 3,969,366 7/1976 Wade .................. 544/366
4,147,700 4/1979 Hirai et al. .................. 548/262

Primary Examiner—Donald G. Daus
Assistant Examiner—S. A. Gibson
Attorney, Agent, or Firm—Lawrence T. Welch

[57] ABSTRACT

The present invention provides certain substituted-piperazinyl-1,2,4-triazoles which are useful for the treatment of sensitized humans for allergies and anaphylactic reactions.

29 Claims, No Drawings

SUBSTITUTED PIPERAZINYL-1,2,4-TRIAZOLES

CROSS REFERENCE TO RELATED APPLICATION

This application is a divisional of copending application Ser. No. 187,920, filed Sept. 17, 1980, now issued as U.S. Pat. No. 4,338,453.

BACKGROUND OF THE INVENTION

The present invention relates to novel substituted 1,2,4-triazoles. More particularly, the present invention relates to substituted piperazinyl-1,2,4-triazoles. The use and preparation of these compounds is described in U.S. Pat. No. 4,338,453, which is expressly incorporated herein by reference.

PRIOR ART

Various 1,2,4-triazoles are known. These compounds have been described as useful for a wide range of uses. Known 1,2,4-triazole compounds include 1-(substituted alkyl)-3,5-bis-pyridyl-1,2,4-triazoles which are stated to be useful as antiasthma and antiallergic agents as described in Netherlands Patent Application 06067 (abstracted by Derwent Farmdoc CPI No. 86573V/50); certain substituted 1,2,4-triazoles useful as antihyperuricacidemic, diuretic, and hypotensive agents as described in U.S. Pat. Nos. 4,102,889, 3,882,134 and 4,111,944; and 5-substituted-alkylamino-1,2,4-triazoles useful as antiinflammatory agents as described in Belgian Pat. No. 875846 (abstracted in Derwent Farmdoc CPI. No. 72003C/41). 3-Benzylidinehydrazino-1,2,4-triazoles useful as hypotensives are also known as described in Belgian Pat. No. 856356 (abstracted in Derwent Farmdoc CPI No. 02073A/02). U.S. Pat. No. 3,910,943 discloses certain 2-[3,5-disubstituted-4H-triazol-4-yl]benzhydrol compounds having CNS activity.

SUMMARY OF THE INVENTION

The present invention particularly provides a compound according to Formula I

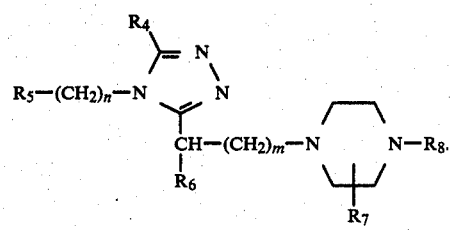

or a pharmacologically acceptable salt thereof,
wherein m is zero, one, 2 or 3;
wherein n is zero, one or 2,
wherein $R_4$ is:
  (a) hydrogen;
  (b) alkyl of one to three carbon atoms, inclusive;
  (c) $R_{54}OCH_2$—, wherein $R_{54}$ is defined below;
  (d) —$CH(R_{35})(OH)$;
  (e) —$R_{35}$;
  (f) —SH;
  (g) $S(O)_qR_{17}$, wherein q is zero, one, or two, and $R_{17}$ is as defined below;
  (h) 1-hydroxy-1-cyclohexyl; or
  (i) 1-cyclohexen-1-yl;

wherein $R_5$, $R_{15}$, $R_{25}$ and $R_{35}$ are the same or different and are
  (i) 2,3, or 4 pyridinyl, or
  (ii) phenyl substituted by zero to 2 chloro, fluoro, bromo, alkyl of from one to 3 carbon atoms, or alkoxy of from one to 3 carbon atoms, or
  (iii) phenyl substituted by one trifluoromethyl and zero to one of the previous phenyl substituents,
wherein $R_6$ is:
  (a) hydrogen;
  (b) —$OR_{54}$;
  (c) alkanoyloxy of from one to 3 carbon atoms; or
  (d) alkyl of from one to 3 carbon atoms; with the proviso that when m is zero, $R_6$ does not contain oxygen;
wherein $R_7$ is
  (i) hydrogen,
  (ii) methyl,
  (iii) phenylmethyl, or
  (iv) 2-phenylethyl,
wherein $R_8$ is:
  (i) —$R_{15}$;
  (ii) —$CH_2R_{15}$, or
  (iii) —$CHR_{15}R_{25}$;
wherein $R_{17}$ is methyl, phenyl, benzyl, or 2-phenylethyl; and
wherein $R_{54}$ is hydrogen or alkyl of one to 3 carbon atoms;
or an enantiomer (when $R_4$ is —$CH(R_{35})OH$ or when $R_6$ is not hydrogen) or diastereomer (when $R_4$ is —$CH(R_{35})OH$ and $R_6$ is not hydrogen) of such compound.

DESCRIPTION OF THE PREFERRED EMBODIMENTS

The present invention particularly provides:

1-(2-Methoxyphenyl)-4-[3-(4-phenyl-4H-1,2,4-triazol-3-yl)propyl]piperazine;
1-[4-fluorophenyl-4-[3-(4-phenyl-4H-1,2,4-triazol-3-yl)propyl]piperazine;
1-Phenyl-4-[3-(4-phenyl)-4H-1,2,4-triazol-3-yl)-propyl]piperazine;
1-(4-Fluorophenyl)-4-[3-(5-methyl-4-phenyl)-4H-1,2,4-triazol-3-yl)propyl]piperazine;
1-(4-Chlorophenyl)-4-[3-(4-phenyl-4H-1,2,4-triazol-3-yl)propyl]piperazine;
1-[2-(5-Methyl-4-phenyl-4H-1,2,4-triazol-3-yl)ethyl]-4-phenylpiperazine;
1-(4-Fluorophenyl)-4-[2-(5-methyl-4-phenyl-4H-1,2,4-triazole-3-yl)ethyl]piperazine;
1-(4-Chlorophenyl)-4-[2-(5-methyl-4-phenyl-4H-1,2,4-triazol-3-yl)ethyl]piperazine;
1-(2-Chlorophenyl)-4-[3-(4-phenyl-4H-1,2,4-triazol-3-yl)propyl]piperazine, dihydrochloride;
1-(3-Chlorophenyl)-4-[3-(4-phenyl-4H-1,2,4-triazol-3-yl)propyl]piperazine;
1-(4-Methoxyphenyl)-4-[3-(4-phenyl-4H-1,2,4-triazol-3-yl)propyl]piperazine;
1-(2-Methylphenyl)-4-[3-(4-phenyl-4H-1,2,4-triazol-3-yl)propyl]piperazine;
1-(4-Fluorophenyl)-4-[3-[4-(4-fluorophenyl)-4H-1,2,4-triazol-3-yl]propyl]piperazine;
1-[3-[4-(4-Fluorophenyl)-4H-1,2,4-triazol-3-yl]propyl]-4-phenylpiperazine;
1-(4-Chlorophenyl)-4-[3-[4-(4-fluorophenyl)-4H-1,2,4-triazol-3-yl]propyl]piperazine;

1-[3-[4-(4-Fluorophenyl)-4H-1,2,4-triazol-3-yl]-propyl]-4-(4-methoxyphenyl)piperazine;

1-(Phenylmethyl)-4-[3-(4-phenyl-4H-1,2,4-triazol-3-yl)propyl]piperazine;

1-(Diphenylmethyl)-4-[3-(4-phenyl-4H-1,2,4-triazol-3-yl)propyl]piperazine; and

1-[3-[5-(Methylthio)-4-phenyl-4H-1,2,4-triazole-3-yl]propyl]-4-phenyl-piperazine.

The most preferred compound of this invention is 1-(diphenylmethyl)-4-[3-(4-phenyl-4H-1,2,4-triazol-3-yl)propyl]piperzine.

I claim:

1. A compound according to formula I

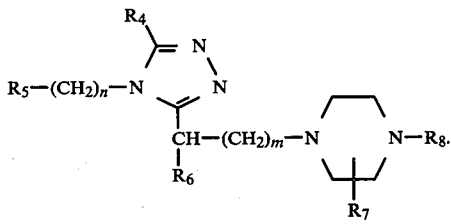

or a pharmacologically acceptable salt thereof,
wherein m is zero, one, 2 or 3;
wherein n is zero, one or 2,
wherein $R_4$ is:
(a) hydrogen;
(b) alkyl of one to three carbon atoms, inclusive;
(c) $R_{54}OCH_2—$, wherein $R_{54}$ is defined below;
(d) $—CH(R_{35})(OH)$;
(e) $—R_{35}$;
(f) $—SH$;
(g) $S(O)_qR_{17}$, wherein q is zero, one, or two, and $R_{17}$ is as defined below;
(h) 1-hydroxy-1-cyclohexyl; or
(i) 1-cyclohexen-1-yl;
wherein $R_5$, $R_{15}$, $R_{25}$ and $R_{35}$ are the same or different and are
(i) 2,3, or 4 pyridinyl, or
(ii) phenyl substituted by zero to 2 chloro, fluoro, bromo, alkyl of from one to 3 carbon atoms, or alkoxy of from one to 3 carbon atoms, or
(iii) phenyl substituted by one trifluoromethyl and zero to one of the previous phenyl substituents,
wherein $R_6$ is:
(a) hydrogen;
(b) $—OR_{54}$;
(c) alkanoyloxy of from one to 3 carbon atoms; or
(d) alkyl of from one to 3 carbon atoms; with the proviso that when m is zero, $R_6$ does not contain oxygen;
wherein $R_7$ is
(i) hydrogen,
(ii) methyl,
(iii) phenylmethyl, or
(iv) 2-phenylethyl,
wherein $R_8$ is:
(i) $—R_{15}$;
(ii) $—CH_2R_{15}$, or
(iii) $—CHR_{15}R_{25}$;
wherein $R_{17}$ is methyl, phenyl, benzyl, or 2-phenylethyl; and wherein $R_{54}$ is hydrogen or alkyl of one to 3 carbon atoms;

or an enantiomer (when $R_4$ is $—CH(R_{35})OH$ or when $R_6$ is not hydrogen) or diastereomer (when $R_4$ is $—CH(R_{35})OH$ and $R_6$ is not hydrogen) of such compound.

2. A compound of claim 1, wherein n is zero and $R_6$ and $R_7$ are hydrogen.

3. 1-(2-Methoxyphenyl)-4-[3-(4-phenyl-4H-1,2,4-triazol-3-yl)propyl]piperazine, a compound of claim 2.

4. A compound of claim 2, wherein m is 2.

5. 1-[4-Fluorophenyl-4-[3-(4-phenyl-4H-1,2,4-triazol-3-yl)propyl]piperazine, a compound of claim 4.

6. 1-Phenyl-4-[3-(4-phenyl-4H-1,2,4-triazol-3-yl)propyl]piperazine, a compound of claim 4.

7. 1-(4-Fluorophenyl)-4-[3-(5-methyl-4-phenyl-4H-1,2,4-triazol-3-yl)propyl]piperazine, a compound of claim 4.

8. 1-(4-Chlorophenyl)-4-[3-(4-phenyl-4H-1,2,4-triazol-3-yl)propyl]piperazine, a compound of claim 4.

9. A compound of claim 2, wherein m is one or two, and $R_4$ is hydrogen, methyl, hydroxymethyl, $S(O)_qR_{17}$ wherein q is zero, or $—CH(R_{35})—(OH)$, wherein $R_5$ and $R_{35}$ are phenyl substituted by zero to 2 chloro, fluoro or bromo.

10. 1-[2-(5-Methyl-4-phenyl-4H-1,2,4-triazol-3-yl)ethyl]-4-phenylpiperazine, a compound of claim 9.

11. 1-(4-Fluorophenyl)-4-[2-(5-methyl-4-phenyl-4H-1,2,4-triazole-3-yl)ethyl]piperazine, a compound of claim 9.

12. 1-(4-Chlorophenyl)-4-[2-(5-methyl-4-phenyl-4H-1,2,4-triazol-3-yl)ethyl]piperazine, a compound of claim 9.

13. A compound of claim 8, wherein $R_5$ is phenyl.

14. 1-(2-Chlorophenyl)-4-[3-(4-phenyl-4H-1,2,4-triazol-3-yl)propyl]piperazine, dihydrochloride, a compound of claim 13.

15. 1-(3-Chlorophenyl)-4-[3-(4-phenyl-4H-1,2,4-triazol-3-yl)propyl]piperazine, a compound of claim 13.

16. 1-(4-Methoxyphenyl)-4-[3-(4-phenyl-4H-1,2,4-triazol-3-yl)propyl]piperazine, a compound of claim 13.

17. 1-(2-Methylphenyl)-4-[3-(4-phenyl-4H-1,2,4-triazol-3-yl)propyl]piperazine, a compound of claim 13.

18. A compound of claim 12, wherein $R_4$ is methyl.

19. A compound of claim 12, wherein $R_4$ is hydrogen.

20. 1-(4-Fluorophenyl)-4-[3-[4-(4-fluorophenyl)-4H-1,2,4-triazol-3-yl]propyl]piperazine, a compound of claim 19.

21. 1-[3-[4-(4-Fluorophenyl)-4H-1,2,4-triazol-3-yl]propyl]-4-phenylpiperazine, a compound of claim 19.

22. 1-(4-Chlorophenyl)-4-[3-[4-(4-fluorophenyl)-4H-1,2,4-triazol-3-yl]propyl]piperazine, a compound of claim 19.

23. 1-[3-[4-(4-Fluorophenyl)-4H-1,2,4-triazol-3-yl]propyl]-4-(4-methoxyphenyl)piperazine, a compound of claim 19.

24. A compound of claim 13, wherein $R_6$ is hydrogen.

25. A compound of claim 1, wherein $R_4$ is hydrogen.

26. 1-(Phenylmethyl)-4-[3-(4-phenyl-4H-1,2,4-triazol-3-yl)-propyl]piperazine, a compound of claim 25.

27. 1-(Diphenylmethyl)-4-[3-(4-phenyl-4H-1,2,4-triazol-3-yl)propyl]piperazine, a compound of claim 25.

28. A compound of claim 1, wherein $R_4$ is methyl or thiomethyl.

29. 1-[3-[5-(Methylthio)-4-phenyl-4H-1,2,4-triazole-3-yl]propyl]-4-phenyl-piperazine, a compound of claim 28.

* * * * *